United States Patent
Mühlbauer

(10) Patent No.: US 6,858,236 B2
(45) Date of Patent: Feb. 22, 2005

(54) PLANT EXTRACTS FOR THE TREATMENT OF INCREASED BONE RESORPTION

(75) Inventor: Roman Conrad Mühlbauer, Rapperswil (CH)

(73) Assignee: Universitat Bern, Bern (CH)

(*) Notice: Subject to any disclaimer, the term of this patent is extended or adjusted under 35 U.S.C. 154(b) by 0 days.

(21) Appl. No.: 10/424,072

(22) Filed: Apr. 25, 2003

(65) Prior Publication Data

US 2003/0203051 A1 Oct. 30, 2003

Related U.S. Application Data

(63) Continuation of application No. 09/825,113, filed on Apr. 3, 2001, now abandoned, which is a continuation of application No. PCT/EP99/07328, filed on Oct. 4, 1999.

(30) Foreign Application Priority Data

Oct. 5, 1998 (GB) ............................................. 9821671

(51) Int. Cl.$^7$ ............................................. A61K 35/78
(52) U.S. Cl. ........................ 424/777; 424/725; 424/779
(58) Field of Search ............................ 424/195.1, 725, 424/177, 779

(56) References Cited

U.S. PATENT DOCUMENTS

| | | | | |
|---|---|---|---|---|
| 4,717,578 A | * | 1/1988 | Biller et al. ................ | 426/589 |
| 5,817,351 A | | 10/1998 | DeWille et al. | |
| 6,214,812 B1 | | 4/2001 | Karpeisky | |
| 6,312,467 B1 | | 11/2001 | McGee | |

FOREIGN PATENT DOCUMENTS

| EP | 0 397 232 | 11/1990 |
|---|---|---|
| EP | 0 600 544 A1 | 6/1994 |
| WO | WO 9704661 | 2/1997 |

OTHER PUBLICATIONS

Ahuja, A. My Struggle to Die with Dignity; The Times, London Mar. 1998, p. 16 (pp. 1–3 printed from ProQuest web site).*

Balch et al., "Prescription For Nutritional Healing", Avery Publishing, Garden City Park, New York, pp. 413–418, (Aug. 1997).

Derwent Abstract XP–002127068.

Gilbert et al., "Determination of Acrylonitrile Monomer in Food Packaging Materials and in Foods", Food Chemistry, vol. 9, pp. 243–252 , pp. 303–306, (1982).

Muhlbauer et al., "Effect of Vegetables on Bone Metabolism", Nature, vol. 401, pp. 343–344, 1999.

Rebiere, Christian Jean Pierre, Abstract only FR2732347, 1996.

Tottori et al., Abstract only JP620761571, 1987.

Mühlbauer et al., "A method for continual monitoring of bone resorption in rats; evidence for a diurnal rhythm", Am J. Physiol., vol. 259, pp. R679–R689, (1990).

* cited by examiner

*Primary Examiner*—Patricia Leith
(74) *Attorney, Agent, or Firm*—John W. Kung; Gary M. Lobel

(57) ABSTRACT

The present invention is concerned with nutritional or pharmaceutical compositions containing an extract or concentrate of a plant from the genus *Lycopersicon*. The compositions of the invention are useful for the treatment or prophylaxis of diseases or conditions which are characterized by increased bone resorption, such as Paget's disease, tumor-induced bone disease or particularly osteoporosis.

3 Claims, No Drawings

PLANT EXTRACTS FOR THE TREATMENT OF INCREASED BONE RESORPTION

This is a continuation of application Ser. No. 09/825,113, filed Apr. 3, 2001 now abandoned, which is a continuation of the National Stage of International Application No. PCT/EP99/07328, filed Oct. 4, 1999, both of which are hereby incorporated by reference in their entirety.

The present invention relates to nutritional or pharmaceutical compositions comprising extracts or concentrates of plants of the genus *Lycopersicon* and their use as inhibitors of bone resorption.

The most common metabolic bone disorder is osteoporosis. Osteoporosis can be generally defined as the reduction in the quantity of bone, either from the reduction in bone formation or the acceleration of bone resorption, in either event the result is a decrease in the amount of skeletal tissue. Osteoclasts (bone resorbing cells) are responsible for the excavation of a portion of bone during the resorption process. After resorption, osteoblasts (bone forming cells) appear, which then refill the resorbed portion with new bone.

In young healthy adults, the rate at which the osteoclasts and osteoblasts are formed and operate maintains a balance between bone resorption and bone formation. However, as normal consequence of aging, an imbalance in this remodeling process develops, resulting in loss of bone. As imbalance continues over time, the reduction in bone mass and thus bone strength leads to fractures.

Many compositions and methods are described in the medical literature for the treatment of osteoporosis. For example, estrogens, calcitonin and bisphosphonates are known to be effective inhibitors of bone resorption.

It has now surprisingly been found that products derived from plants of the genus *Lycopersicon* (tomato) have a potent inhibitory effect on bone resorption.

The present invention therefore foresees the use of an extract or concentrate from a plant of the genus *Lycopersicon* in the preparation of a pharmaceutical or nutritional composition for the treatment or prophylaxis of a disease or condition which is characterized by increased bone resorption, such as Paget's disease, tumor-induced bone disease or particularly osteoporosis.

Also provided is a method for the treatment or prophylaxis of a disease or condition which is characterized by increased bone resorption, such as Paget's disease, tumor-induced bone disease or particularly osteoporosis, comprising the administration of a pharmaceutical or nutritional composition to a human or other mammal, said pharmaceutical or nutritional composition comprising an extract or concentrate from a plant of the genus *Lycopersicon*, in an amount which is effective for inhibiting bone resorption.

The invention further provides the use of an extract or concentrate from a plant of the genus *Lycopersicon* in the preparation of a pharmaceutical or nutritional composition for one or more indications from the following group:

a) inhibiting bone resorption,
b) reducing the risk of developing a disease or condition which is characterized by increased bone resorption, such as Paget's disease, tumor-induced bone disease or particularly osteoporosis,
c) for supporting the treatment of a disease or condition which is characterized by increased bone resorption, such as Paget's disease, tumor-induced bone disease or particularly osteoporosis,
d) for supporting the treatment of osteoporosis, and
e) for reducing the risk of developing osteoporosis.

Further provided is a method for
a) inhibiting bone resorption,
b) reducing the risk of developing a disease or condition which is characterized by increased bone resorption, such as Paget's disease, tumor-induced bone disease or particularly osteoporosis,
c) for supporting the treatment of a disease or condition which is characterized by increased bone resorption, such as Paget's disease, tumor-induced bone disease or particularly osteoporosis,
d) for supporting the treatment of osteoporosis, and/or
e) for reducing the risk of developing osteoporosis
comprising the administration of a pharmaceutical or nutritional composition to a human or other mammal, said pharmaceutical or nutritional composition comprising an extract or concentrate from a plant of the genus *Lycopersicon*, in an amount which is effective for inhibiting bone resorption.

Osteoporosis as used herein includes osteoporosis induced by hormone deficiency (e.g. postmenopausal) and old age, as well as secondary osteoporosis such as osteoporosis secondary to steroid treatment or secondary to malnutrition caused by anorexia nervosa.

Preferably the concentrate or extract is derived from a plant the botanical species *Lycopersicon esculentum* (also referred to as *Lycopersicon lycopersicum*, "tomato"), *Lycopersicon pimpinellifolium* ("Current tomato"), *Lycopersicon hirsutum*, *Lycopersicon peruvianum*, *Lycopersicon parviflorum* and/or *Lycopersicon pennellii* ("Fuzzy tomato"), whereby *Lycopersicon esculentum* is preferred.

The plant extracts and concentrates of the invention are preferably obtained from an edible portion of the plant. By edible portion is meant the portion which is consumed by humans in either raw or cooked form.

The extracts and concentrates of the above-mentioned plants may be in liquid form or in solid form such as in granulate or powder form.

Suitable plant concentrates are obtainable e.g. by drying or freeze-drying the fresh-cut plants or the respective roots, fruits or seeds thereof and then optionally grinding or granulating the dried material; or by squeezing the fresh-cut plants or the respective roots, fruits or seeds thereof and gathering the liquid fraction and optionally drying it, or by cooking the fruit until a concentrated thickened paste is obtained. The use of a concentrate of the above-mentioned plants in solid form and particularly in powder form is preferred, however, also commercial forms such as tomato juice, ketchup, tomato sauce or tomato paste are useful plant concentrates according to the invention.

Suitable methods of obtaining extracts of the above-mentioned plants are known in the art. The plant extracts are obtainable e.g. by extracting the fresh-cut or dried plants or the respective roots, fruits or seeds thereof for example with water or with one or more food grade solvents or with a mixture of water and one or more food grade solvents. Suitable food grade solvents include propane, butane, butyl acetate, ethyl acetate, ethanol, carbon dioxide, acetone, nitrous oxide, methanol and propan-2-ol, whereby ethanol and carbon dioxide are preferred; ethanol is a particularly preferred food grade solvent. After the extraction step the liquid phase is optionally concentrated or dried by evaporation or freeze drying. The fresh-cut or dried plant material may be introduced in cold or preferably hot water and/or solvent, preferably water or a mixture of water with one or more solvents, for a specified period of time, which may vary within wide ranges depending on the kind of plant material or solvent used but commonly amounts for example to 1 to 30 minutes, preferably 2 to 15 minutes and most preferred 5 to 10 minutes for a water extraction and for example 30 to 90 minutes, preferably 60 minutes for an ethanol/water extraction. For a water extraction the temperature preferably lies in the range of 85 to 95° C. and for an alcohol/water extraction the temperature preferably lies in the range of 55 to 65° C. For a carbon dioxide extraction, the extraction preferably takes place at 0 to 40° C. and at super-critical pressure (e.g. 80–200 bar). After the extraction the liquid phase is separated and advantageously concentrated or evaporated to dryness according to known methods. To obtain a concentrated extract two or more extraction steps as described above may be combined. Moreover, the plant extracts may be obtained by introducing the fresh-cut or dried plant in water and subjecting the mixture to a steam distillation. The distillate is collected and is then advantageously concentrated or evaporated to dryness.

The extract may be used in liquid form, particularly in aqueous form, or in solid form, particularly in granulate or powder form. If the extract is in liquid form, it has a solid contents of for example from 1 to 25% by weight, preferably from 2 to 20% by weight and most preferred from 2 to 15% by weight.

The amount of inventive plant extract or concentrate to be supplied may vary within wide ranges, depending on i.a. the desired treatment, subject to be treated and his needs. Thus, where the subject to be treated is an adult person (typically of ca. 60 to 75 kg body weight), a satisfactory inhibitory effect on bone resorption is, in general obtained with compositions formulated to allow a daily administration of 0.1 to 20 grams, preferably 0.2 to 15 grams, and most preferred 0.4 to 10 grams of plant concentrate or extract (on a solvent-free basis).

Suitable nutritional compositions comprising the above-mentioned plant extracts or concentrates represent a further object of the invention. They are characterized in that they comprise (a) at least one extract or concentrate from a plant of the genus *Lycopersicon,*
(b) a calcium source, and optionally
(c) at least one energy source selected from the group consisting of carbohydrate, fat and nitrogen sources, and optionally
(d) Vitamin D.

The term nutritional compositions as used herein comprises i.a.:

i) Dietary foods for special medical purposes (hereinafter "medical nutrition") which means a category of foods for particular nutritional uses specially processed or formulated and intended for the dietary management of patients and to be used under medical supervision which are intended for exclusive or partial feeding of patients with a limited, impaired or disturbed capacity to take, digest, absorb, metabolise or excrete ordinary foodstuffs or certain nutrients contained therein or metabolites, or with other medically determined nutrient requirements, whose dietary management cannot be achieved only by modification of the normal diety, by other foods for particular nutritional uses or by a combination of the two. These foods are either nutritionally complete foods with a nutrient-adapted formulation specific for a disease, disorder or medical condition which, used in accordance with the manufacturer's instructions, may constitute the sole source of nourishment for the persons for whom they are intended or they may be nutritionally incomplete foods with a nutrient-adapted formulation for a disease, disorder or medical condition which are not suitable to be used as the sole source of nourishment and are thus used as a partial replacement or as a supplement to the patient's diet;

ii) Food products which are likely to be classified as "functional foods", i.e. foods that are similar in appearance to conventional foods and are intended to be consumed as part of a normal diet or a supplement, but have been modified to physiological roles beyond the provision of simple nutrient requirements. The term food products is intended to cover the whole variety of foods and beverages, including but not limited to yoghurts, ice creams, cheeses, baked products such a fresh or frozen bread, crisp bread, crisp bread sandwiches, biscuits and cakes, dairy and dairy substitute foods, desserts, confectionary products, edible oil compositions, spreads, cereal and/or fruit bars, breakfast cereals, savoury snacks, juices, soups, ketch-up and the like.

Preferred nutritional compositions comprise component (c) as a mandatory ingredient. Particularly preferred nutritional compositions comprise both component (c) and (d) as mandatory ingredients.

Regarding component (a), the definitions, preferences and amounts given before for the extracts and concentrates of a plant from the genus *Lycopersicon* apply. It is also possible to have a mixture of two or more of said plant extracts and concentrates as component (a). The nutritional compositions of the invention conveniently comprise (in % by weight) for example from approximately 0.1 to 40%, preferably from approximately 3 to 25% and most preferred from 5 to 15% of plant extract or concentrate component (a).

The calcium source (b) may comprise any physiological acceptable inorganic or organic compound containing calcium. Examples are inorganic calcium salts, for example calcium chloride, calcium phosphate, calcium sulfate, calcium oxide, calcium hydroxide or calcium carbonate, or organic calcium components like whole or skim milk powder, calcium caseinate or calcium salts of organic acids such as calcium citrate, calcium maleate, or mixtures thereof. The use of organic calcium compounds, particularly skim milk powder, calcium caseinate or mixtures thereof, as calcium source (b) is preferred. The amount of calcium component to be supplied may vary within wide ranges. In general, the inventive compositions comprise in one unit dosage from about 100 mg to 1000 mg, preferably 200 mg to 700 mg and most preferred 300 to 600 mg of calcium (on an elemental basis).

The nutritional compositions of the invention conveniently comprise (in % by weight) for example from approximately 1 to 60%, preferably from approximately 5 to 50% and most preferred from 10 to 40% of calcium component (b).

Suitable carbohydrate sources include for example maltodextrins, starch, lactose, glucose, sucrose, fructose, xylit and/or sorbit. In these forms the carbohydrates are both energy suppliers and sweeteners. The inventive compositions may contain one or more different carbohydrate sources.

Suitable fat sources include omega-6 polyunsaturated fatty acid sources, omega-3 polyunsaturated fatty acid sources, mono-unsaturated fatty acid sources, medium chain fatty acid sources (i.e. $C_6$–$C_{12}$-fatty acids); or mixtures thereof. The above-mentioned fatty acids may be employed in each case in form of the free acid, in mono-, di- or particularly in triglyceride form, or in form of a pharmacological or nutritional acceptable natural source.

Suitable natural sources of omega-6 polyunsaturated fatty acids include vegetable oils such as safflower oil, sunflower oil, soya oil, cotton oil and corn oil. Suitable natural sources of omega-3 polyunsaturated fatty acids include linseed oil and fish oils such as menhaden oil, salmon oil, mackerel oil, tuna oil codliver oil and anchovy oil.

Suitable natural sources of mono-unsaturated fatty acid sources are particularly omega-9 mono-unsaturated fatty acids, for example olives, canola, safflower (hybrids) and sunflower (hybrids).

A preferred fat source comprises triglyceride oils supplying the desired amounts of omega-6 polyunsaturated fatty acids and omega-3 polyunsaturated fatty acids and which are rich in the medium chain fatty acid residues (i.e. residues of $C_6$–$C_{12}$ fatty acid) and/or mono-unsaturated fatty acid residues. The inventive compositions may contain one or more different fat sources.

Examples of suitable nitrogen sources of the inventive nutritional compositions include sources containing nutritionally acceptable proteins such as soy bean derived proteins; milk proteins such as whey proteins or caseinates; and/or protein hydrolysates; and/or essential amino acids mixtures in free amino acid form or salt form; and/or compounds associated with the synthesis of polyamines, such as arginine, arginine precursors, ornithine and the like, in free amino acid form or salt form.

Preferred nitrogen sources of the nutritional compositions are (i) soy bean derived proteins, which may be employed in the form of soy beans or in the form of any suitable soja extract or concentrate, for example in form of soy flour, dried soy sprouts, soybean milk, or as dried aqueous extract from soybeans; or (ii) milk proteins, for example whey derived proteins or caseinates which may be employed for example in the form of whey powder, caseinate salts such as calcium caseinate and/or whole or preferably skim milk powder and/or (iii) a mixture of essential amino acids and/or (iv) arginine as nitrogen source.

Milk proteins such as whey powder, caseinates, particularly calcium caseinate, and/or skim milk powder are another particularly preferred nitrogen source of the claimed nutritional compositions. The inventive compositions may contain one or more different nitrogen sources.

The nutritional compositions comprise (in % by weight) for example, from approximately 0.1% to 98.9%, preferably from approximately 1 to approximately 95%, and most preferred from 10 to 90% of energy source component (c).

The contribution of the nitrogen source, carbohydrate source and fat source to the caloric of the inventive nutritional compositions may vary within wide ranges. For example, the carbohydrate source provides for 30 to 70% of the total energy supply, the nitrogen source for 5 to 45%, preferably 5 to 40%, and the fat source for 0.1 to 15%, or 0.01 to 5%, of the total energy supply of the composition. In preferred compositions of the invention the carbohydrate source provides for 40 to 60% of the total energy supply, the nitrogen for 20 to 35% and the fat source for 3 to 12% of the total energy supply of the composition.

A preferred energy source (c) of the inventive compositions comprises 30 to 70% of the total energy supply of one or more carbohydrate sources selected from the group consisting of maltodextrins, starch, lactose, glucose, sucrose, fructose, xylit and sorbit;

5 to 45% of the total energy supply of one or more nitrogen sources selected from the group consisting of soy bean derived proteins, milk proteins, a mixture of essential amino acids and arginine and 0.1 to 15% of the total energy supply of one or more fat sources comprising omega-3- and omega-6-polyunsaturated fatty acids.

A particularly preferred energy source (c) of the inventive compositions comprises 40 to 60% of the total energy supply of one or more carbohydrate sources selected from the group consisting of maltodextrins, starch, lactose, glucose, sucrose, fructose, xylit and sorbit; 20 to 35% of the total energy supply of one or more nitrogen sources selected from the group consisting of soy bean derived proteins, skim milk powder and caseinates; and 3 to 12% of the total energy supply of one or more fat sources comprising omega-3- and omega-6-polyunsaturated fatty acids.

The amount of Vitamin D (optional component (d)) to be supplied may vary within wide ranges. In general, the inventive compositions comprise in one unit dosage from about 50 IU to 1000 IU, preferably about 100–500 IU (more particularly preferred about 500 IU for a medical nutrition product and about 200 IU for a functional food product).

The nutritional compositions of the invention may comprise other nutritionally acceptable components such as vitamins, minerals, trace elements, fibers (preferably soluble fibers), flavors, preservatives, colorants, sweeteners, emulsifiers and the like.

Examples of vitamins suitable for the incorporation in the composition of the invention include Vitamin A, Vitamin D, Vitamin E, Vitamin K, Vitamin C, folic acid, thiamin, riboflavin, Vitamin $B_6$, Vitamin $B_{12}$, niacin, biotin and panthotenic acid in pharmaceutical or nutritionally acceptable form.

Examples of mineral elements and trace elements suitable for the incorporation in the composition of the invention include sodium, potassium, phosphorous, magnesium, copper, zinc, iron, selenium, chromium and molybdenum in pharmaceutical or nutritionally acceptable form.

The term soluble fiber as used herein refers to fibers which are able to substantially undergo fermentation in the colon to produce short chain fatty acids. Examples of suitable soluble fibers include agar-agar, alginates, carubin, carrageenan, gum arabic, guar gum, karaya gum, locust bean gum, pectin, tragacanth, cereal beta-glucan or xanthan gum. They may be hydrolysed or not.

Suitable flavors include natural or artificial flavors, for example fruit flavors such as banana, orange, peach, pineapple or rasberry; vegetable flavors; or vanilla, cocoa, chocolate, coffee and the like.

Preferred ingredients of the inventive nutritious compositions in addition to components (a), (b), (c) and (d) comprise beta-carotene (Vitamin A), Vitamin E, Vitamin C, thiamin, Vitamin $B_1$, $B_6$ and/or $B_{12}$, potassium, magnesium, selenium, zinc, phosphorous and soluble fiber in pharmaceutical or nutritionally acceptable form.

The nutritional compositions may comprise (in % by weight) for example, from approximately 0.1% to 15%, preferably from approximately 0.2 to approximately 10%, and most preferred from 0.5 to 5% of these additional components other than components (a), (b), (c) and optionally (d).

The nutritional compositions defined as medical nutrition may be formulated and administered in any form suitable for enteral administration, for example oral administration or tube feeding, e.g. nasal administration. The medical nutrition compositions are conveniently administered in the form of an aqueous liquid. The medical nutrition compositions suitable for enteral application are accordingly preferably in aqueous form or in powder or granulate form, whereby the powder or granulate is conveniently added to water prior to use. For use as tube feeding, the amount of water to be added will i.a. depend on the patient's fluid requirements and condition.

The inventive medical nutrition compositions may be in form of a complete formula diet (in liquid or powder form), such that, when used as sole nutrition source essentially all daily caloric, nitrogen, fatty acids, vitamin, mineral and trace element requirements are met. In general, the daily amount to be supplied to adult persons will lie in the range of 750 to 3500 kcal/day, in particular of 1000 to 2000 kcal/day. However, the inventive medical nutrition compositions are preferably intended for use as a medical nutrition supplement. The amount of energy supplied by a supplement should not be too excessive, in order not to unnecessarily suppress the patients appetite. The supplement conveniently comprises energy sources in an amount supplying from 50 to 1500 kcal/day, preferably 100 to 900 kcal/day and most preferred 150 to 700 kcal/day.

Preferred functional foods according to the invention as defined hereinbefore are drinks (vegetable or juice), savoury snacks (such as savoury cereal bars and extruded snacks) and spreads which may be obtained in a manner known per se.

The nutritional compositions of the invention which are in liquid form, for example in drink form, or preferably in solid form, for example in granulate or powder form, may be obtained in a manner known per se, e.g. by admixing the ingredients and optionally adding water.

The invention further relates to pharmaceutical compositions in single dose unit form comprising (a) at least one extract or concentrate from a plant of the genus *Lycopersicon*, and (b) a pharmaceutical acceptable carrier.

These pharmaceutical compositions are compositions for enteral administration, such as oral, nasal or rectal administration. Suitable pharmaceutical compositions may be in liquid form or preferably in solid form and comprise (in % by weight) for example, from approximately 0.001% to 100%, preferably from approximately 0.1 to approximately 50%, active ingredient (a).

The active ingredient (a) is an extract or concentrate from a plant of the genus *Lycopersicon* where the above-given definitions and preferences apply. It is also possible to have a mixture of two or more of said plant extracts and concentrates a).

Pharmaceutical compositions for enteral administration are, for example, those in single dose unit forms, such as dragées, tablets, capsules or sachets. They are prepared in a manner known per se, for example by means of conventional mixing, granulating, confectioning, dissolving or lyophilising processes.

For example, pharmaceutical compositions for oral administration can be obtained by combining the active ingredient with solid carriers, optionally granulating a resulting mixture and processing the mixture or granules, if desired or necessary after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, and, if desired, disintegrators, such as the above-mentioned starches, and also carboxymethyl starch, cross-linked polyvinylpyrrolidone, agar, or alginic acid or a salt thereof, such as sodium alginate. Excipients are especially flow-conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical compositions are hard gelatin capsules and also soft, sealed capsules consisting of gelatin and a plasticiser, such as glycerol or sorbitol. The hard gelatin capsules may comprise the active ingredient in the form of granules, for example in admixture with fillers, such as lactose, binders, such as starches, and/or glidants, such as talc or magnesium stearate, and, if desired, stabilisers. In soft capsules the active ingredient is preferably dissolved or suspended in suitable liquids, such as fatty oils, paraffin oil or liquid polyethylene glycols, it is likewise being possible to add stabilisers.

Suitable rectally administrable pharmaceutical compositions are, for example, suppositories that consist of a combination of the active ingredient with a suppository base material. Suitable suppository base materials are, for example, natural or synthetic triglycerides, paraffin hydrocarbons, polyethylen glycols or higher alkanols. It is also possible to use gelatin rectal capsules which comprise a combination of the active ingredient with a base, material. Suitable base materials are, for example, liquid triglycerides, polyethylenglycols or paraffin hydrocarbons.

The inhibitory effect on bone resorption of the inventive plant extracts and concentrates may be assessed by measuring the urinary excretion of [$^3$H]-tetracycline from chronically prelabled rats as described in R. C. Mühlbauer and H. Fleisch, Am J Physiol 258, R 679–R689 (1990). The method is based on the characteristics (i) that $^3$H-labeled tetracycline is deposited in hard tissues during their formation; and (ii) when bone is resorbed, [$^3$H]-tetracycline is released, circulates in blood, and is excreted into the urine where it can be assessed by counting $^3$H. This is probably due to the fact that [$^3$H]-tetracycline from bone circulates in a form that binds poorly to hydroxyapatite and, therefore, [$^3$H]-tetracycline once liberated from bone, is only poorly reutilized during bone turnover, and because of an efficient renal excretion. The method may be performed as follows: rats are injected subcutaneously twice a week with increasing volumes of a solution containing [$^3$H]-tetracycline starting shortly after birth until the age of about six weeks. At the age of about 50 days, the animals are transferred to individual metabolic cages and every rat is fed with the same amount of a standardized diet for about the three weeks. After that, one group of rats is fed with a purified diet, and another group is fed with the purified diet containing in addition a certain amount of an inventive plant concentrate or extract. During the experiments, the animals have free access to demineralized water. When the rats are about 60 days old, daily 24-hour urine collections are started, and the $^3$H contents in urine are determined by liquid scintillation counting. A diagram is then prepared wherein the [$^3$H]-tetracycline contents in urine of the two groups of rats are plotted as a function of time (days).

Experiments show that the plant extracts and concentrates of the invention are capable of considerably decreasing the cumulative [$^3$H]-tetracycline excretion in urine of intact male rats which indicates a high inhibitory effect on bone resorption. Accordingly, the claimed nutritional and pharmaceutical compositions are useful for the treatment and prophylaxis of all kinds of diseases or conditions which are characterized by increased bone resorption, such as Paget's disease, tumor-induced bone disease or particularly osteoporosis.

The inhibitory effect of the plant extracts or concentrates on bone resorption may also be assessed by an in vitro assay in which ivory slices, onto which freshly isolated osteoclasts have been settled, are incubated with a medium containing the extract or concentrate to be tested. The inhibitory effect on osteoclasts is assessed by counting the osteoclast resorption pits on the ivory slice.

In the following Examples, which illustrate the invention, % are parts by weight unless stated otherwise, and temperatures are given in ° C.

EXAMPLE 1

The following is an example of a suitable composition of an inventive medical nutrition supplement in powder form.

| Supplement in Powder Form (1 portion) | |
|---|---|
| Content | |
| Inventive Concentrate[1] | 65.0 g |
|  | 14.5 g |
| including carbohydrates, protein and fiber | |
| Protein | 20.0 g |
| including | |
| Ca-caseinate protein | 8.7 g |
| skim milk powder | 11.0 g |
| Fat | 2.8 g |
| including | |
| omega-6 polyunsaturated acids | 1.3 g |
| omega-3 polyunsaturated acids | 0.03 g |
| Carbohydrates (including inventive extract) | 31.0 g |
| including | |
| lactose | 16.5 g |
| maltodextrin | 3.5 g |
| Fiber (soluble) | 5.0 g |
| Further ingredients | 3.0 g |
| including | |
| Na | 230 mg |
| K | 500 mg |
| Ca | 600 mg |
| Mg | 90 mg |
| P | 430 mg |
| Cl | 350 mg |
| Zn | 150 mg |
| Retinol (vitamin A) | 0.3 mg |
| Calciferol (vitamin D) | 5.0 mcg |
| Tocopherol (vitamin E) | 3.0 mg |
| Phylloquinone (vitamin K1) | 30.0 mcg |
| Thiamin (vitamin B1) | 0.4 mg |
| Riboflavin (vitamin B1) | 0.5 mg |
| Pyridoxine (vitamin B6) | 0.8 mg |
| Cyanocobalamin (vitamin B12) | 0.8 mcg |
| Ascorbic acid (vitamin C) | 20.0 mg |
| Biotin | 50.0 mcg |
| Folic acid | 120.0 mcg |
| Niacinamide | 5.0 mg |
| Panthothenic acid | 2.0 mg |
| Energy value | 229 kcal |

[1]The inventive concentrate is obtained by drying 250 g fresh tomato and grinding the dried tomato to a fine powder.

The above supplement may be mixed with water and taken in appropriate concentration between meals.

EXAMPLE 2

The following is an example of a suitable composition of an inventive Functional Food in the form of a cereal bar.

| Cereal Bar (1 portion = 2 bars of 32 g) | |
|---|---|
| Content | |
| Inventive concentrate[1] | 64.0 g |
|  | 14.5 g |
| Sorbitol | 11.2 g |
| Palm Oil | 4.9 g |
| Cornflake Crumbs | 6.0 g |
| Rolled Oats | 6.0 g |
| Crisp Rice | 6.0 g |
| Gelatin | 7.0 g |
| Soy protein | 7.0 g |
| Na-chloride | 0.7 g |
| Ca | 0.5 g |
| Mg | 0.2 g |
| Calciferol (vitamin D) | 5.0 mcg |

[1]The inventive concentrate is obtained by drying 250 g fresh tomato and grinding the dried tomato to a fine powder..

EXAMPLE 3

Effect of Tomato Concentrate on Bone Resorption

The measurement of the effect of the inventive plant extracts and concentrates on bone resorption is based on a method as described in R. C. Mühlbauer and H. Fleisch, Am J Physiol 259, R 679–R689 (1990). Bone resorption is monitored by the urinary excretion of $^3$H in Wistar rats prelabled from birth for 6 weeks with [$^3$H]-tetracycline as described in the above-mentioned reference. The rats are then housed in individual metabolic cages and are fed for 10 days with a standard laboratory chow (Kliba 331, Klingentalmühle, Kaiseraugst, Switzerland) containing 1.0 g Ca, 0.7 g P, and 80 IU of vitamin $D_3$/100 g of food. After this adaptation period, all rats receive a diet containing 1.0 g Ca, 1.2 g P, and 80 IU of vitamin $D_3$/100 g dry weight. This is achieved by adding appropriate amounts of Ca-gluconate and neutral phosphate salts to a basic low calcium, low phosphate diet (Sodi 2134, Klingenthalmühle, Kaiseraugst, Switzerland) in powder form for another 10 days during which urine is collected. Then rats are "pair-fed" receiving 28 g of wet food per day. One group (n=5) is switched to a purified diet ("Diet P", Sodi 2160, Klingenthalmühle, Kaiseraugst, Switzerland given as wet food with a water content of 45±2% containing 1.0 g Ca, 1.2 g P, and 80 IU of vitamin $D_3$/100 g dry weight), a second group (n=5) is fed with the purified diet containing in exchange for 1 g of diet 1 g ground dry tomato per day (corresponding to 17.2 gram of fresh tomato) and a third group (n=5) is fed with the purified diet containing in exchange for 1 g of diet 1 g ground dry onions per day (corresponding to 8.1 g fresh onions).

After 10 days adaptation without urine collection and a further 10 days with urine collection, the rats are allocated to the different treatment groups. Using the baseline 24 hour [$^3$H]-tetracycline excretion as selection criterion, special care is taken to obtain similar mean initial values for each group. Thereafter, the rats are switched to the purified diet with or without inventive concentrate and daily 24-hour urine collections are performed over a period of 10 days, and the cumulative [$^3$H]-tetracycline excretion in urine is determined by liquid scintillation counting.

After 10 days of treatment the cumulative inhibition of bone resorption was 15%±4 and 26%±4, in rats daily fed the ground and dried tomato and onion respectively, measured as counts per minute of the control over counts per minute of the tomato and onion group. Both values for the dry tomato and dry onion fed groups were clearly outside the confidence interval of the control group. In other words, both dried tomato and dried onions showed significant inhibition of bone resorption. In the same set-up, the values for groups fed 1 g dry soy, 1 g dry carrot or 1 g skim milk powder were not outside the confidence interval, i.e. these ingredients did not show a significant inhibition of bone resorption at the dosage of 1 g per day.

What is claimed is:

1. A method for decreasing bone resorption caused by a disease or condition which causes bone resorption comprising administering to a mammal including a human, in need thereof, a concentrate from a plant of the genus *Lycopersicon*, in an effective amount for inhibiting bone resorption wherein said concentrate is obtained by a process selected from the group consisting of:

a. drying or freeze-drying the plant and grinding or granulating said dried or freeze-dried plant, and b. squeezing the plant to obtain a liquid fraction and drying said liquid fraction, wherein said concentrate is administered in an amount of 0.1 to 20 grams per day.

2. The method of claim 1 wherein said disease or condition is Paget's disease, tumor inducing bone disease or osteoporosis.

3. The method of claim 1 wherein said plant is selected from the group consisting of *Lycopersicon esculentum, Lycopersicon pimpinellifolium, Lycopersicon hirsutum, Lycopersicon peruvianum, Lycopersicon paviflorum* and *Lycopersicon pennellii*.

* * * * *